(12) United States Patent
Faghih et al.

(10) Patent No.: US 11,622,744 B2
(45) Date of Patent: Apr. 11, 2023

(54) SYSTEM AND METHOD FOR AUTOMATED OVARIAN FOLLICULAR MONITORING

(71) Applicants: Massachusetts Institute of Technology, Cambridge, MA (US); The General Hospital Corporation, Boston, MA (US)

(72) Inventors: Rose T. Faghih, Houston, TX (US); Emery N. Brown, Brookline, MA (US); Aaron K. Styer, Westwood, MA (US)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 463 days.

(21) Appl. No.: 16/629,210

(22) PCT Filed: Jul. 7, 2017

(86) PCT No.: PCT/US2017/041111
§ 371 (c)(1),
(2) Date: Jan. 7, 2020

(87) PCT Pub. No.: WO2019/009919
PCT Pub. Date: Jan. 10, 2019

(65) Prior Publication Data
US 2020/0129139 A1    Apr. 30, 2020

(51) Int. Cl.
*A61B 8/08*    (2006.01)
*G06T 7/136*    (2017.01)
(Continued)

(52) U.S. Cl.
CPC ............ *A61B 8/085* (2013.01); *A61B 8/5207* (2013.01); *G06T 7/0012* (2013.01); *G06T 7/12* (2017.01);
(Continued)

(58) Field of Classification Search
CPC ... A61B 8/085; A61B 8/5207; A61B 2503/40; G06T 7/0012; G06T 7/12; G06T 7/136;
(Continued)

(56) References Cited

U.S. PATENT DOCUMENTS

| 7,071,199 | B1 * | 7/2006 | Hirst | .................... | C07D 487/04 |
| | | | | | 514/263.2 |
| 2003/0083563 | A1 * | 5/2003 | Katsman | ............ | H04N 1/32529 |
| | | | | | 600/407 |

(Continued)

OTHER PUBLICATIONS

Hiremath et al, ("Automated ovarian classification in digital ultrasound images", Int. J. Biomedical Engineering and Technology, vol. 11, No. 1, 2013, p. 46-65) (Year: 2013).*

(Continued)

*Primary Examiner* — Amara Abdi
(74) *Attorney, Agent, or Firm* — Wolf, Greenfield & Sacks, P.C.

(57) ABSTRACT

Methods and products for automated real-time ovarian follicular detection, monitoring and analysis are provided. The devices and methods allow for remote or local analysis, while minimizing or eliminating the need for technician review of the output images. The methods are useful in human and non-human subjects including companion animals and other animals such as endangered species.

27 Claims, 6 Drawing Sheets

(51) Int. Cl.
    *G06T 7/12*     (2017.01)
    *G06T 7/155*     (2017.01)
    *G16H 40/67*     (2018.01)
    *G16H 30/40*     (2018.01)
    *G06T 7/00*     (2017.01)

(52) U.S. Cl.
    CPC .............. *G06T 7/136* (2017.01); *G06T 7/155* (2017.01); *G16H 30/40* (2018.01); *G16H 40/67* (2018.01); *A61B 2503/40* (2013.01); *G06T 2207/10132* (2013.01); *G06T 2207/20036* (2013.01); *G06T 2207/30004* (2013.01)

(58) Field of Classification Search
    CPC ........... G06T 7/155; G06T 2207/10132; G06T 2207/20036; G06T 2207/30004; G06T 7/149; G06T 2207/10016; G06T 2207/20076; G06T 2207/20081; G06T 2207/20116; G06T 2207/20152; G06T 2207/20192; G16H 30/40; G16H 40/67
    See application file for complete search history.

(56) References Cited

U.S. PATENT DOCUMENTS

| | | | | |
|---|---|---|---|---|
| 2013/0051674 | A1* | 2/2013 | Goossens | G06T 7/10 382/173 |
| 2013/0184584 | A1* | 7/2013 | Berkey | A61B 8/5292 600/441 |
| 2014/0193051 | A1* | 7/2014 | Lee | G06T 7/0012 382/128 |
| 2017/0091914 | A1* | 3/2017 | Halmann | A61B 8/4245 |
| 2017/0103518 | A1* | 4/2017 | Murphy | A61B 8/08 |
| 2017/0116497 | A1* | 4/2017 | Georgescu | G06N 3/08 |
| 2018/0330518 | A1* | 11/2018 | Choi | G16H 30/20 |

OTHER PUBLICATIONS

Ajitha et al, (Ultrasound Image Despeckling using Singular Value Decomposition, Dec. 10-12, 2015, IEEE, pp. 82-86) (Year: 2015).*
International Search Report and Written Opinion dated Oct. 10, 2017, for Application No. PCT/US2017/041111.
International Preliminary Report on Patentability dated Jan. 16, 2020, for Application No. PCT/US2017/041111.
Ata et al., Ultrasound automated volume calculation in reproduction and in pregnancy. Fertil Steril. Jun. 2011;95(7):2163-70. doi: 10.1016/j.fertnstert.2011.04.007. Epub May 5, 2011.
Aja-Fernandez et al., On the estimation of the coefficient of variation for anisotropic diffusion speckle filtering. IEEE Trans Image Process. Sep. 2006;15(9):2694-701.
Chan et al., Active contours without edges. IEEE Trans Image Process. 2001;10(2):266-77.
Chatap et al., A survey on various classification techniques for medical image data. Int J Comp Appl. Jul. 2014; 97(15): 0975-8887.
Gerris et al., Self-operated endovaginal telemonitoring versus traditional monitoring of ovarian stimulation in assisted reproduction: an RCT. Hum Reprod. Sep. 2014;29(9):1941-8. doi: 10.1093/humrep/deu168. Epub Jul. 3, 2014.
Gomez et al., Detection of Follicles in Ultrasounds Videos of Bovine Ovaries. Iberoamerican Congress on Pattern Recognition. Nov. 8, 2016. pp. 352-359.
Hiremath et al., Follicle detection and ovarian classification in digital ultrasound images of ovaries. Advancements and Breakthroughs in Ultrasound Imaging. IntechOpen. 2013.
Hu et al., New Perspectives on Criteria for the Determination of HCG Trigger Timing in GnRH Antagonist Cycles. Medicine (Baltimore). May 2016;95(20):e3691.
Khalid et al., Amenorrhoea and polycystic ovarian syndrome. Ultrasound and Endoscopic Surgery in Obstetrics and Gynaecology. 2003; 221-6.
Kirikutha et al., Automatic segmentation of ovarian follicle using K-means clustering. ICSIP, 2014 5th Int Conf. 2014; 137-41.
Lebbi et al., The significance of monitoring folliculogenesis. IvfLite. Jun. 2015; 2(1): 6-13.
Li et al., Distance regularized level set evolution and its application to image segmentation. IEEE Trans Image Process. Dec. 2010;19(12):3243-54. doi: 10.1109/TIP.2010.2069690. Epub Aug. 26, 2010. Erratum in: IEEE Trans Image Process. Jan. 2011;20(1):299.
Meyer, Topographic distance and watershed lines. Signal Processing. 1994; 38: 113-125.
Potocnik et al., Computerized detection and recognition of follicles in ovarian ultrasound images: a review. Med Biol Eng Comput. Dec. 2012;50(12):1201-12. doi: 10.1007/s11517-012-0956-y. Epub Sep. 26, 2012.
Potocnik et al., Improved prediction-based ovarian follicle detection from a sequence of ultrasound images. Comput Methods Programs Biomed. Mar. 2003;70(3):199-213.
Rabiu et al., A review on computer assisted follicle detection techniques and polycystic ovarian syndrome (PCOS) diagnostic systems. IJCTT. Oct. 2015; 28(1): 41-5.
Rosenfeld et al., Sequential operations in digital picture processing. J ACM Oct. 1966; 13(4): 471-94.
Subhamathi, Ultrasound image despeckling using singular value decomposition. 2015 IEEE Recent Advances in Intelligent Computational Systems (RAICS). Dec. 10, 2015. pp. 82-86.
Tegnoor, Automated ovarian classification in digital ultrasound images using SVM. Int J Eng Res Tech. Aug. 2012; 1(6): 1-17.

\* cited by examiner

 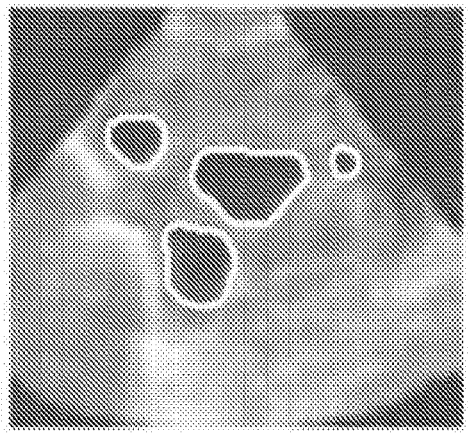
FIG. 2A　　　　　　　　FIG. 2B
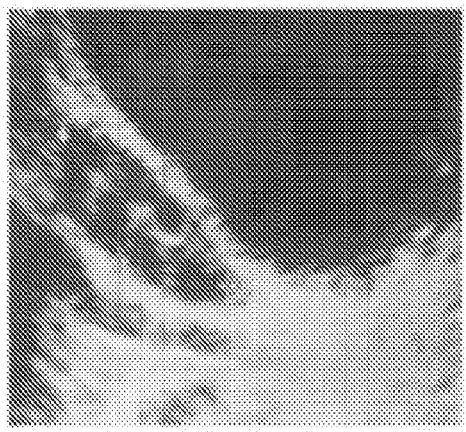 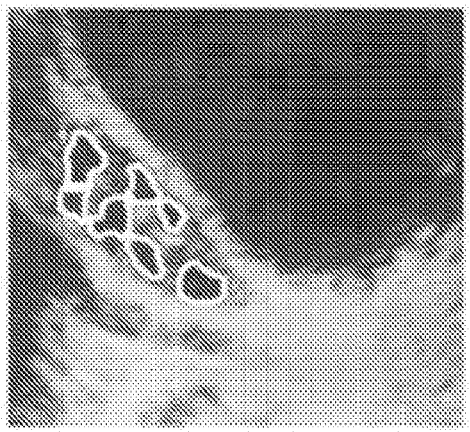
FIG. 3A　　　　　　　　FIG. 3B

SYSTEM AND METHOD FOR AUTOMATED OVARIAN FOLLICULAR MONITORING

RELATED APPLICATION

This application is a national stage filing under 35 U.S.C. § 371 of international PCT application, PCT/US2017/041111, filed Jul. 7, 2017, entitled "SYSTEM AND METHOD FOR AUTOMATED OVARIAN FOLLICULAR MONITORING," the content of which is incorporated herein by reference in its entirety.

BACKGROUND OF THE INVENTION

Ultrasonography is a non-invasive imaging modality of obstetrics and gynecology [1]. In reproductive medicine, transvaginal ultrasound examination is primarily used for monitoring follicular growth during ovarian stimulation and for estimating ovarian reserve [2]. The number and size of ovarian follicles, number of antral follicles (follicles that are 2-8 mm in average diameter) [3], and growth rate of dominant follicles (follicles that are larger than 10 mm in average diameter) [4] are the primary endpoints of measurement for ovarian follicle monitoring [2]. Ovarian follicular monitoring is essential for guiding the amount and duration of medications for ovarian stimulation, ovulation induction and intrauterine insemination, controlled ovarian hyperstimulation for oocyte (egg) retrieval, in vitro fertilization (IVF) and fresh embryo transfer, egg donation cycles, and for women who electively freeze their eggs or embryos for future use. However, there are multiple limiting factors in the ovarian follicular monitoring clinical practice. Performing ultrasound scans every 2-3 days is necessary to optimize ovarian response, the yield of eggs, and the ultimate success of an IVF cycle. Since measuring follicles is done manually and requires multiple visits, it becomes tremendously inconvenient given the number of examinations that need to be done at fertility centers and hospitals [5]. Additionally, fertility treatment is not feasible for some couples who live in rural areas far away from fertility centers. Moreover, ultrasound images analyzed by different technicians or medical experts can lead to inconsistent results and interpretations [6]. Hence, automated follicular monitoring has the great potential to maximize pregnancy success of IVF treatment on a large scale. Despite the clinical need for automated follicular monitoring, fully automated computerized follicular monitoring has not yet been achieved.

SUMMARY OF THE INVENTION

In some aspects, a principled image processing framework that can facilitate automated ovarian follicular monitoring for real-time use in clinical practice and home-based monitoring is provided. Computerized follicle detection is currently either semi-automated or has low performance due to multiple limiting factors: (1) noise, (2) detecting multiple follicles very close to each other as one follicle region without finding the boundary of individual follicles, and (3) not being fast enough to be used in real-time clinical practice. To overcome the current limitations, we first combine methods from image processing and linear algebra to remove noise and reduce redundancy while maintaining significant parts of the ultrasound image. Moreover, to ensure fully automated follicle detection, we use a highly innovative adaptive segmentation technique based on various features of the image (such as pixel intensity level) and features of the detected follicle areas (such as roundness). This approach allows for rapid identification and measurement of individual follicles with the ability to differentiate between the borders of adjacent follicles and the boundary between the follicle and ovarian stroma.

To overcome the existing limitations, we combine methods from image processing and linear algebra to remove noise and reduce redundancy while maintaining significant parts of the ultrasound image. Moreover, instead of only using one segmentation technique, the follicles have been detected by utilizing various segmentation techniques depending on features of the image (such as pixel intensity level) and features of the detected follicle areas (such as roundness). The hybrid segmentation methods may utilize three different segmentation techniques: (1) a time-dependent PDE method for automatic detection of interior contours which can locate follicle boundaries in presence of lighter pixels at follicle borders, (2) a gradient flow PDE approach for handling topological changes efficiently and representing complex topology contours that can be applied to images that are not very dark for robust segmentation, (3) gradient flow approach for reaching a local minimum (which represents a segment) that can be used to differentiate between the borders of adjacent follicles.

Some aspects of the present disclosure include a method of real-time ovarian follicular detection in a subject, comprising obtaining ovarian ultrasound images of the subject's ovarian follicles using an ultrasound device, analyzing the ovarian ultrasound images with a segmentation algorithm to produce a fully annotated ultrasound image without manual input to allow for real-time ovarian follicular detection. In some embodiments, the subject is a human subject. In some embodiments, the subject is of reproductive age. In some embodiments, the subject is undergoing a procedure comprising ovarian stimulation, ovulation induction, intrauterine insemination, controlled ovarian hyperstimulation, oocyte retrieval, in vitro fertilization, or embryo transfer.

In another embodiment, the fully annotated ultrasound image includes identification and measurement of individual follicles and differentiates between the borders of adjacent follicles.

In other embodiments, the real time detection detects and measures all ovarian follicles in one ultrasound image in less than 30 seconds. In another embodiment, the real time detection detects and measures all ovarian follicles in one ultrasound image in less than seconds.

In some embodiments, the method of obtaining ovarian ultrasound images is performed by the subject remotely. In another embodiment, the fully annotated ultrasound images are delivered to a health care provider.

In some embodiments, the algorithm involves analysis of the ovarian ultrasound images, by at least one processor, by producing a grayscale intensity image, producing a compressed image from the grayscale image, applying an anisotropic diffusion scheme for multiplicative speckle to reduce the speckle noise of the compressed image, rescaling and thresholding the compressed image to obtain a binary mask image, and performing morphological processing on the binary mask to obtain a morphologically processed mask. In some embodiments, the method further comprises labeling connected components in the morphologically processed mask. In some embodiments, the method further comprises measuring properties of the morphologically processed mask, checking the properties of the labeled image regions to decide whether the labeled image region should be labeled as a follicle by considering physical constraints on some of the properties of the image region and generating a final binary mask that only includes image regions that are labeled as follicles and storing the properties of each of the labeled follicles.

In other embodiments, the production of the compressed image is performed using singular value decomposition on the grayscale image to produce the compressed image. In another embodiment, singular value decomposition is performed by calculating an explained variance for all possible approximation ranks in terms of a ratio of the Frobenius norm of a k-rank approximation matrix to a Frobenius norm of a full image matrix, wherein the k-rank approximation matrix that has the lowest rank among all approximation matrices that have an explained variance above a threshold is selected as a low rank approximation for obtaining the compressed image.

In another embodiment, anisotropic diffusion scheme is used with adaptive noise estimation over a square window.

In another embodiment, when areas that are close to the follicle border are lighter than areas of the follicle further away from the follicle border an active contour method is used to create a second binary mask and wherein the second binary mask is combined with the binary mask image.

In other embodiments, morphological processing includes image dilation, followed by filling interior gaps, removing connected objects on follicle border, eroding the image, and removing small regions.

In some embodiments, when the ovarian ultrasound images that are not very dark, the ovarian ultrasound images and the morphologically processed mask are inputted to a distance regularized level set evolution formulation, wherein the morphologically processed mask is an initial level set function to be updated by level set evolution, and wherein the obtained updated level set function after level set evolution is converted to a binary image. In some embodiments, the level set evolution is derived as a gradient flow that minimizes an energy functional with a distance regularization term and an external energy that drives motion of a zero level set toward desired locations.

In other embodiments, the distance regularization term has a double-well potential function which forces the gradient magnitude of the level set function a minimum point.

In some embodiments the method further comprises distance transforming white areas having area threshold properties in the binary image mask using a Chebyshev distance transform to perform watershed segmentation and produce an output, wherein the pixels having highest gradient magnitude intensities represent follicle region boundaries and gradient of an image flows along a path to finally reach a local minimum which represents a segment and wherein the output of the watershed segmentation and the white areas in the binary image mask that are less than the area threshold properties are combined to generate a watershed segmented binary image.

In some embodiments, the subject has a reproductive condition or does not have a reproductive condition or infertility but is seeking elective fertility treatment for fertility preservation (e.g. oocyte and/or embryo cryopreservation). In other embodiments, the reproductive condition is due to infections, cancer, physical damage, or hormonal imbalances. In another embodiment, the reproductive condition comprises premature ovarian failure (POF), ovarian torsion, or polycystic ovarian syndrome (PCOS).

In some embodiments, the subject is a non-human animal. In one embodiment, the non-human animal is a companion animal. In some embodiments, the companion animal is selected from the group consisting of dogs, cats, and horses. In another embodiment, the non-human animal is an exotic animal. In one embodiment, the exotic animal is selected from the group consisting of elephants, pandas and zebras.

In some embodiments, the method further comprises measuring serum estrogen, anti-Mullerian hormone, progesterone, or testosterone levels in the subject. In some embodiments, the ovarian follicles detected have a size range of 2-8 mm. In other embodiments, the ovarian follicles detected have a size range of 9-22 mm. In some embodiments, the ultrasound device for obtaining the ovarian ultrasound images includes a probe and wherein an angle of the probe with respect to the imaged ovarian follicles is measured.

Some aspects of the present disclosure include at least one computer-readable storage medium storing computer-executable instructions that, when executed, perform a method for automatic detection of ovarian follicles by analyzing an ovarian follicular ultrasound image, the method comprising receiving the ovarian follicular ultrasound image obtained from a subject; determining, measuring and labeling, by at least one processor, individual follicles within the ovarian follicular ultrasound image, wherein the individual follicles are differentiated from adjacent follicles, wherein the individual follicles are determined, measured and labeled by converting the ovarian follicular ultrasound image to a grayscale intensity image, compressing the grayscale intensity image using a singular value decomposition to form a compressed image, reducing speckle noise of the compressed image to produce a reduced noise image, processing the reduced noise image to produce a binary mask image, performing morphological processing of the binary mask image to obtain a morphologically processed mask, and labeling and measuring follicles imaged within the morphologically processed mask to produce a fully annotated ultrasound image, and performing automatic detection of ovarian follicles at least in part by analyzing at least the fully annotated ultrasound image without manual input.

In some embodiments, processing of the binary mask image includes rescaling and thresholding or a supervised learning step.

In other embodiments, the follicles are labelled in measured image regions.

Some aspects of the present disclosure include at least one computer-readable storage medium storing computer-executable instructions that, when executed, perform a method for automatic detection of ovarian follicles by analyzing an ovarian follicular ultrasound image, the method comprising receiving the ovarian follicular ultrasound image obtained from a subject; determining, measuring and labeling, by at least one processor, individual follicles within the ovarian follicular ultrasound image, wherein the individual follicles are differentiated from adjacent follicles, wherein the individual follicles are determined, measured and labeled by converting the ovarian follicular ultrasound image to a grayscale intensity image, compressing the grayscale intensity image using a singular value decomposition to form a compressed image, reducing speckle noise of the compressed image to produce a reduced noise image, processing the reduced noise image to produce a binary mask image, performing morphological processing on the binary mask image to obtain a morphologically processed mask, and labeling and measuring follicles imaged within the morphologically processed mask to produce a fully annotated ultrasound image, and performing automatic detection of ovarian follicles at least in part by analyzing at least the fully annotated ultrasound image without manual input. In some embodiments the computer-readable storage medium is on a smartphone, tablet or computer.

In yet other aspects, the invention is an automated follicular detection sonogram system having an imaging sensor for obtaining an ultrasound image, sequence of ultrasound images or ultrasound video of an ovary of a subject, at least one computer-readable storage medium storing computer-executable instructions that, when executed, perform a method for automatic detection of ovarian follicles by analyzing an ultrasound image, sequence of ultrasound images or ultrasound video, the method comprising: receiving the ultrasound image, sequence of ultrasound images or ultrasound video obtained from a subject; determining, measuring and labeling, by at least one processor, individual follicles within the ultrasound image, sequence of ultrasound images or ultrasound video, wherein the individual follicles are differentiated from adjacent follicles, wherein the individual follicles are determined, measured and labeled by converting the ultrasound image, sequence of ultrasound images or ultrasound video to a grayscale intensity image, compressing the grayscale intensity image using a singular value decomposition to form a compressed image, reducing speckle noise of the compressed image to produce a reduced noise image, processing the reduced noise image to produce a binary mask image, performing morphological processing on the binary mask image to obtain a morphologically processed mask, and labeling and measuring follicles imaged within the morphologically processed mask to produce a fully annotated ultrasound image, images or video, and performing automatic detection of ovarian follicles at least in part by analyzing at least the fully annotated ultrasound image, images or video without manual input.

Other aspects of the present disclosure include an automated follicular detection sonogram system comprising an imaging sensor for obtaining an ultrasound image, sequence of ultrasound images or ultrasound video of an ovary of a subject, a storage device for storing the ultrasound image, sequence of ultrasound images or ultrasound video locally or remotely, and at least one computer-readable storage medium storing computer-executable instructions that, when executed, perform automated detection and measurement of ovarian follicles within the stored ultrasound image, sequence of ultrasound images or ultrasound video to produce a fully annotated ultrasound image.

In some embodiments, the system further comprises a transmitter for transmitting the fully annotated ultrasound image to a remote device. In some embodiments, the automated follicular detection sonogram system is a home ultrasound device. In other embodiments, the automated follicular detection sonogram system is portable.

In some embodiments, the imaging sensor is an ultrasound device for obtaining the ultrasound images wherein the device includes a probe. In another embodiment, the ultrasound device includes a component for measuring and storing an angle of the probe with respect to each image captured by the ultrasound device.

In some embodiments, the automated detection and measurement of ovarian follicles within the stored ultrasound image, sequence of ultrasound images or ultrasound video is processed by determining, measuring and labeling individual follicles within the ultrasound image, wherein the individual follicles are differentiated from adjacent follicles, wherein the individual follicles are determined, measured and labeled by converting the ultrasound image to a grayscale intensity image, compressing the grayscale intensity image using a singular value decomposition to form a compressed image, reducing speckle noise of the compressed image to produce a reduced noise image, processing the reduced noise image to produce a binary mask image, performing morphological processing on the binary mask image to obtain a morphologically processed mask, and labeling and measuring follicles imaged within the morphologically processed mask to produce a fully annotated ultrasound image.

In another embodiment, the follicles in the sequence of ultrasound images or ultrasound video are tracked using a Kalman filter.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF THE DRAWINGS

FIGS. 2A and 2B depict ultrasound images of Example 1 which show the ultrasound image of the ovary (FIG. 2A) and the detected follicles (FIG. 2B). The ultrasound image of 2A was published in [10] under CC BY 3.0 license.

FIGS. 3A and 3B depict ultrasound images of Example 2 which show the ultrasound image of the ovary (FIG. 3A) and the detected follicles (FIG. 3B). The ultrasound image of 3A was published in [10] under CC BY 3.0 license.

DETAILED DESCRIPTION OF THE INVENTION

Figure 1:
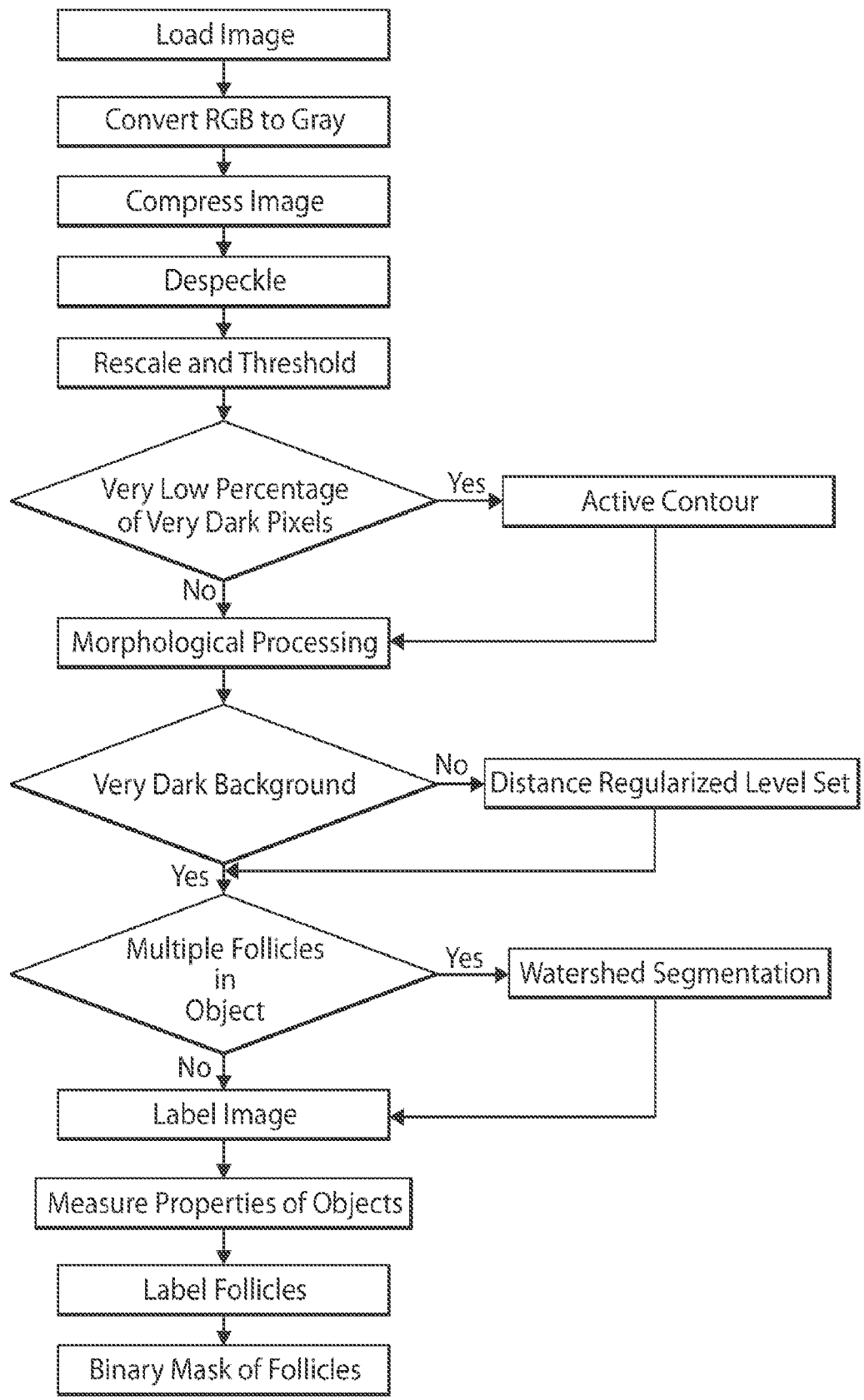
FIG. 1 shows a flowchart, which summarizes the presently claimed novel follicle detection algorithm.

In typically medical image processing, first images are pre-processed and enhanced, then features are extracted and selected, and finally, images are classified and segmented; Chatap et al. provides a table with various techniques used at each step of this process [7]. In 2012, Potocnik et al. reviewed computerized follicle detection and recognition algorithms (both 2-D and 3-D) and pointed out that open challenges in this area of research include lack of fully automated recognition procedures particularly for smaller follicles and high time complexity that is far from real-time operation [5]. They suggest that an automated follicle recognition algorithm that would be acceptable in clinical practice should detect/measure the follicles in less than 30 seconds [5]. Moreover, in 2015 Rabiu et al. reviewed follicle detection techniques as well as polycystic ovarian syndrome diagnostic systems. They pointed out that the performance of the reviewed techniques are often low due to two limiting factors: (1) poor quality of ultrasound images, and (2) limited features extracted [8]. According to their review, the approach by Tegnoor [9] that uses Support Vector Machine (SVM) for classification has the highest follicle detection rate (98.89%). However, the segmentation technique used in this study could lead to over-segmentation and False Acceptance Rate (FAR) due to limitations in handling intensity inhomogeneity on the boundary of follicles [8]. Based on the 2013 review by Hiremath et al., SVM and fuzzy logic have yielded best follicle detection results [10]. In the literature some follicle detection studies follicular regions versus non-follicular regions are detected. However, for follicles that are close to each other while the non-follicular area between them has an intensity level similar to the follicles, the entire regions with follicles is detected together as one follicle and the follicles close to each other are not differentiated as distinct and unique individual follicles. Thus, computerized follicle detection is currently either semi-automated or has low performance due to limiting factors: (1) noise, (2) detecting multiple follicles very close to each other as one follicle region without finding the boundary of individual follicles, and (3) not being fast enough to be used in real-time clinical practice.

The methods and products of the invention have overcome a number of these problems associated with prior art ultrasound analytical techniques. Given that obstetricians and gynecologists use the information about the number and size of each follicle, having a segmentation algorithm, such as those disclosed according to the invention, that detects the borders of each individual follicle and does not detect two follicles as one follicle region will make follicular measurement and monitoring more accurate and consistent.

The fully automated computerized follicle detection system of the invention overcomes these limiting factors and improves the efficiency and precision of ovarian follicular monitoring, optimizing response to ovarian stimulation and pregnancy success. Automated follicular monitoring will have the ability to maximize pregnancy success of IVF treatment on a large scale. Moreover, such a system allows for remote self-operated monitoring of women using home-based sonogram devices. Finally, such a system can reduce the cost of IVF. The methods of the invention will have a significant impact on the clinical practice.

A follicle detection algorithm that overcomes the current limitations in automatic detection of follicles is described herein. Some of the main contributions of the present invention include: (1) A novel speckle noise reduction approach that combines singular value decomposition for image compression with an anisotropic diffusion scheme for multiplicative speckle [12] to reduce the speckle noise; (2) Identification and measurement of individual follicles with the ability to differentiate between the borders of adjacent follicles and the boundary between the follicle and ovarian stroma (supporting tissue); and (3) Detection of follicles in less than 30 seconds.

First, methods from image processing and linear algebra were combined to remove noise and reduce redundancy while maintaining significant parts of the ultrasound image. Moreover, to ensure fully automated follicle detection, a highly innovative hybrid segmentation technique is used based on features of the image (such as pixel intensity level) and features of the detected follicle areas (such as roundness). This approach allows for rapid identification and measurement of individual follicles with the ability to differentiate between the borders of adjacent follicles and the boundary between the follicle and ovarian stroma. In summary, the outcome of this invention has significant potential to shift the current clinical practice to more accurate faster follicular monitoring at the convenience of the patient's home.

Thus, the invention in some aspects includes a method of real-time ovarian follicular detection in a subject. "Real-time ovarian follicular detection" or "real-time detection" as used herein refers to the analysis of images at the time the images are detected. Analysis of the images usually takes place after the images are captured and stored. In order for an automated analysis to occur in real-time the analysis of the ultrasound image should occur 30 seconds or less. In some embodiments of the invention the real time detection detects and measures all ovarian follicles in one ultrasound image in less than or equal to 25, 20, 15, 14, 13, 12, 11, 10, 8, or 5 seconds. In some embodiments of the invention the real time detection detects and measures all ovarian follicles in one ultrasound image in less than or equal to 2.1 seconds, 2.3 seconds, 1.3 seconds, 1.6 seconds or 1.8 seconds.

The method is performed by obtaining ovarian ultrasound images of the subject's ovarian follicles using an ultrasound device. Ultrasound typically includes a console containing a computer and electronics, a video display screen and an imaging sensor or transducer that is used to do the scanning. The imaging sensor is a small hand-held device attached to the scanner by a cord or wireless. The imaging sensor sends out high-frequency sound waves into the body and then listens for the returning echoes from the tissues in the body. The ultrasound image is generated based on information generated by the returning echoes. The raw image is processed as described herein and immediately visible on a video display screen or monitor and/or stored locally or transmitted to another site for viewing and/or storage. The image is created based on the amplitude (loudness), frequency (pitch) and time it takes for the ultrasound signal to return from the area within the patient that is being examined to the imaging sensor, as well as the type of body structure and composition of body tissue through which the sound travels. Ultrasound devices are sold by many companies, including Mobius, which markets portable devices for home use. The algorithms and methods described herein may be used on any available device.

The ovarian ultrasound images obtained using the ultrasound device are raw images. The methods of the invention are useful for processing those images to produce a fully annotated image which can be immediately reviewed to provide input on the subject, without the need for further technical analysis. This process is referred to herein as automated or fully automated because the image is analyzed using the algorithm and methods described herein. Typically when ultrasound images are obtained using prior art methods a technician or health care worker must review and annotate the image in order to distinguish between close follicular borders, the presence of false positives such as cysts and false negatives such as light areas. The algorithm of the invention takes into account all of these features in a real-time manner to produce the fully annotated image. A fully annotated ultrasound image, as used herein is an image in which all of the individual follicles have been identified as discreet entities, including closely situated follicles.

The methods described herein may be performed with an algorithm such as a segmentation algorithm. An exemplary algorithm is shown in FIG. 1 and described in more detail below. In medical image processing, images are first pre-processed and enhanced, then features are extracted and selected, and finally, images are classified and segmented. In this study, instead of only using one segmentation technique, follicles were detected by utilizing various segmentation techniques depending on features of the image (such as pixel intensity level) and features of the detected follicle areas (such as roundness). In summary, to handle noise, a singular value decomposition was performed and a low-rank approximation of the image matrix followed by speckle reducing anisotropic diffusion was obtained. A binary mask of the image was created based on lightness of the image. Moreover, if the image was scanned in a manner such that the areas that are closer to the follicle border are lighter than the rest of the follicle area, the active contour method was used and the resulting mask was combined with the binary mask. Then morphological processing was performed, which is generally done in image processing. Then, based on the pixel intensity of the images, if the images are neither very dark nor very light, a distance regularized level set evolution formulation was used. In some ultrasound images, some follicles are very close to each other and the image intensity between such follicles is very similar to the intensity of the follicles, which can lead to detecting multiple follicles as one larger follicle area. To differentiate between the borders of adjacent follicles and the boundary between the follicle and ovarian stroma, areas detected in the level set binary image that satisfy certain properties (that indicate multiple follicles might have been detected as one follicle area) are distance transformed using a Chebyshev distance transform to perform watershed segmentation and separate any connected regions. Then, the properties of the image regions are measured and the labeled image regions that have properties that match the expected properties of follicles are detected as follicles.

In some embodiments, the ultrasound device for obtaining the ovarian ultrasound images includes a probe and wherein an angle of the probe with respect to the imaged ovarian follicles is measured.

The advantages of this approach over the conventional methods include (1) handling the ultrasound image noise, (2) fully automated recognition of follicles by differentiating between the borders of adjacent follicles and the boundary between the follicle and ovarian stroma, (3) fast detection of follicles (in less than 30 seconds) which can be used in clinical practice, and (4) capturing various features of images and detected regions in images as well as combination of different segmentation techniques, which result in higher quality segmentations. In the future, follicles will be automatically detected from a large dataset of ultrasound images. Since information about the number and size of each follicle and the interval development of follicles is essential to assisting obstetricians-gynecologists in their clinical decision making, the algorithm described herein has the promising potential to be applied in the future to improve the efficiency, precision, and accuracy of ovarian follicular monitoring and to optimize response to ovarian stimulation and pregnancy success following elective fertility treatment.

The method of obtaining ovarian ultrasound images may be performed locally in a hospital or clinic. When performed locally the health care worker may review the fully annotated images in order to provide feedback or diagnosis of the subject in real-time. Alternatively the images may be stored for later review.

An advantage of the methods and systems of the invention is that the ultrasound analysis may be, alternatively, performed by the subject or by another individual remotely. In this instance, the fully annotated ultrasound images may be reviewed and analyzed directly by the user or may be delivered to a health care provider.

In some embodiments, the algorithm involves analysis of the ovarian ultrasound images, by at least one processor, by producing a grayscale intensity image, producing a compressed image from the grayscale image, applying an anisotropic diffusion scheme for multiplicative speckle to reduce the speckle noise of the compressed image, rescaling and thresholding the compressed image to obtain a binary mask image, and performing morphological processing on the binary mask to obtain a morphologically processed mask. In some embodiments, the method further comprises labeling connected components in the morphologically processed mask. In some embodiments, the method further comprises measuring properties of the morphologically processed mask, checking the properties of the labeled image regions to decide whether the labeled image region should be labeled as a follicle by considering physical constraints on some of the properties of the image region and generating a final binary mask that only includes image regions that are labeled as follicles and storing the properties of each of the labeled follicles.

In another embodiment, the fully annotated ultrasound image includes identification and measurement of individual follicles and differentiates between the borders of adjacent follicles.

Examples of tools operating in accordance with techniques explained above are described below, but it should be appreciated that the examples are provided merely for purposes of illustration and that other implementations are possible.

A detailed summary of the exemplary automated follicle detection algorithm shown in FIG. 1 is presented below.

1.) Initially steps are taken to reduce noise and redundancies for fast accurate image processing. Methods from image processing and linear algebra were combined to remove noise and reduce redundancy while maintaining significant parts of the ultrasound image. First, using a singular value decomposition approach from linear algebra, image compression was performed. To do this, the Frobenius-norm-based explained variance was calculated and the compressed image was obtained by choosing the lowest rank approximation matrix with an explained variance above a threshold. For example, an RGB image may be converted to a grayscale intensity image by using the rgb2gray function in MATLAB R2016a which eliminates the hue and saturation while maintaining the luminance. Any other method in any programming language for converting an RGB image to a grayscale intensity image can be used alternatively. Then, singular value decomposition is performed on the grayscale image. For all possible approximation ranks, the explained variance is calculated in terms of the ratio of the Frobenius norm of the k-rank approximation matrix to the Frobenius norm of the full image matrix. The k-rank approximation matrix that has the lowest rank among all the approximation matrices that have an explained variance above a threshold is selected as the low rank approximation for obtaining the compressed image.

2.) Second, based on an anisotropic diffusion scheme for multiplicative speckle, the speckle noise resulting from the head of the ultrasound device not being moist enough was removed. This approach combines minimum mean squared error adaptive filtering methods, partial differential equations (PDE), and image and noise coefficient of variation estimation. The anisotropic diffusion scheme for multiplicative speckle [12] is applied to reduce the speckle noise of the compressed image. In this approach, speckle-reducing anisotropic diffusion with adaptive noise estimation over a square window is used.

3.) Next follicle boundaries are located in the presence of lighter pixels at follicle borders. In some ultrasound images, for some follicles, the areas that are closer to the follicle border are lighter than the rest of the follicle area and when the grayscale image is converted to a binary image, lighter areas of the follicle are not captured as a part of the follicle. To handle such images in the segmentation algorithm of the invention, an active contour method was utilized. Active contour without edges, which is based on curve evolution techniques and can detect objects without depending on the gradient of the image was employed. This approach is a time-dependent PDE approach in which the energy is minimized if the curve is on the boundary of the object. This method allows for automatic detection of interior contours independently of the location of the initial curve in the image, and can successfully locate follicle boundaries in presence of lighter pixels at follicle borders.

4. A binary mask was obtained by rescaling and thresholding the image. In some ultrasound images, for some follicles, the areas that are closer to the follicle border are lighter than the rest of the follicle area and when the grayscale image is converted to a binary image, lighter areas of the follicle are not captured as a part of the follicle. If the percentage of the very dark pixels in a compressed image is very low, the active contour method [13] is used to create a new binary mask. Then, this new binary mask is combined with the binary image obtained in the previous step.

5.) Morphological processing is performed on the binary mask to obtain the morphologically processed mask. Morphological processing includes image dilation, followed by filling interior gaps, removing connected objects on the border, eroding the image, and removing small regions.

6.) Next accurate, robust, and computationally efficient segmentation was performed. To speed up curve evolution for follicle detection while maintaining numerical accuracy, a distance regularized level set evolution approach was utilized. The level set evolution equation for the curve evolution equation is defined by a PDE and is derived as a gradient flow that minimizes an energy functional with a distance regularization term defined with a double-well potential function such that it forces the gradient magnitude of the level set function to one of its minimum points. This approach can handle topological changes efficiently and represent complex topology contours. In the disclosed algorithm, this approach is applied to images that satisfy the required pixel intensity condition and is not implemented on ultrasound images with very dark background. Thus, for images that are not very dark, the RGB image and the morphologically processed mask are then inputted to a distance regularized level set evolution formulation [14] where the morphologically processed mask is the initial level set function to be updated by level set evolution. In this formulation, the level set evolution is derived as the gradient flow that minimizes an energy functional with a distance regularization term and an external energy that drives the motion of the zero level set toward desired locations [14]. The distance regularization term is defined with a double-well potential function such that it forces the gradient magnitude of the level set function to one of its minimum points [14]. The obtained updated level set function after level set evolution is converted to a binary image.

7.) Steps may be taken differentiate between the borders of adjacent follicles. In some ultrasound images, some follicles are very close to each other and the image intensity between such follicles is very similar to the intensity of the follicles, which can lead to detecting multiple follicles as one larger follicle area. To ensure multiple follicles are not detected as one larger follicle area, the white areas in the binary image that satisfy certain properties (e.g. are larger than an area threshold, or have a roundness lower than a threshold) are distance transformed using a Chebyshev distance transform [15] to perform watershed segmentation [16] where the pixels having the highest gradient magnitude intensities represent the region boundaries and gradient of an image flows along a path to finally reach a local minimum which represents a segment. Then, by combining the output of the watershed segmentation and the white areas in the binary image that are smaller than the area threshold, a watershed segmented binary image is generated.

8.) The connected components in binary image are labeled.

9.) The properties of the image regions may be measured by using the region props function in MATLAB R2016a and taking the labeled image and the grayscale image. Any other method in any programming language for measuring the properties of the image regions can be used alternatively.

10.) Various properties of the labeled image regions are checked to decide whether the labeled image region should be labeled as a follicle. This is done by considering constraints (lower and/or upper bounds) on some of the properties of the image region. For example, the centroid of follicles are not expected to be found at the upper corner of the ultrasound image. This can also be done by using classification approaches on various properties of image regions.

11.) A final binary mask that only includes the image regions that are labeled as follicles is created and the properties of each of these follicles are stored.

Accurate and consistent ovarian follicular monitoring is essential to guiding high quality clinical management in reproductive medicine in patients planning or undergoing elective fertility treatment. Automated follicular monitoring is desired as: (1) Measuring follicles manually becomes tremendously inconvenient for a high number of examinations. (2) Ultrasound images analyzed by different experts can lead to different results. The main challenges in automated follicle detection include: (1) poor quality of images due to speckle noise, (2) lack of fully automated recognition procedures particularly for smaller follicles as well as follicles that are close to each other, and (3) high time complexity of existing algorithms.

The system for automated follicle may be tracked in ultrasound image sequences and videos. Follicles may be tracked through a sequence of images by using a Kalman filter. When ultrasound videos of ovaries are used, the frames in the video may be processed as a sequence of images and the follicles tracked using a Kalman filter. To do this, first for each image a final binary mask is created, which will be followed by detecting follicles and obtaining their properties using the follicle detection algorithm. Then, follicle tracking is done through the sequence of images; follicles (groups of connected pixels) detected in the final binary mask of each image in the sequence of images are tracked using a Kalman filter, and the track's location in each image sequence is predicted. Moreover, the likelihood of assignment of each of these detections to each track is determined. In any given image of the sequence, some of these detections will be assigned to tracks, whereas other detections and tracks continue to be unassigned. Using the matching detections, the assigned tracks will be updated, and if tracks are unassigned, they will be marked invisible and a new track will start. Each track will count the number of consecutive images where it continues to be unassigned, and if the count is higher than a threshold, it will be assumed that the follicle left the field of view.

The system of the invention may be an application that automatically detects follicles for clinical practice. Accurate and consistent ovarian follicular monitoring is essential to guiding high quality clinical management in reproductive medicine in patients planning or undergoing elective fertility treatment. The image processing framework may be implemented in the form of a smartphone application which may be used by doctors and medical professionals as an aid to clinical practice. This application can also be used as an aid in teaching imaging in obstetrics and gynecology. Using a home-based ultrasound device, subjects or patients can obtain ultrasound images of their ovaries, and input the images to the smartphone application. The smartphone application detects the follicles and measures the number and size of these detected follicles and can send the results to the doctor. This allows for accessible follicular monitoring in the convenience of the patient's home. Similarly, this application can be used at a fertility clinic to increase the accuracy of follicular monitoring as well as the gynecologists' efficiency.

Figure 7:
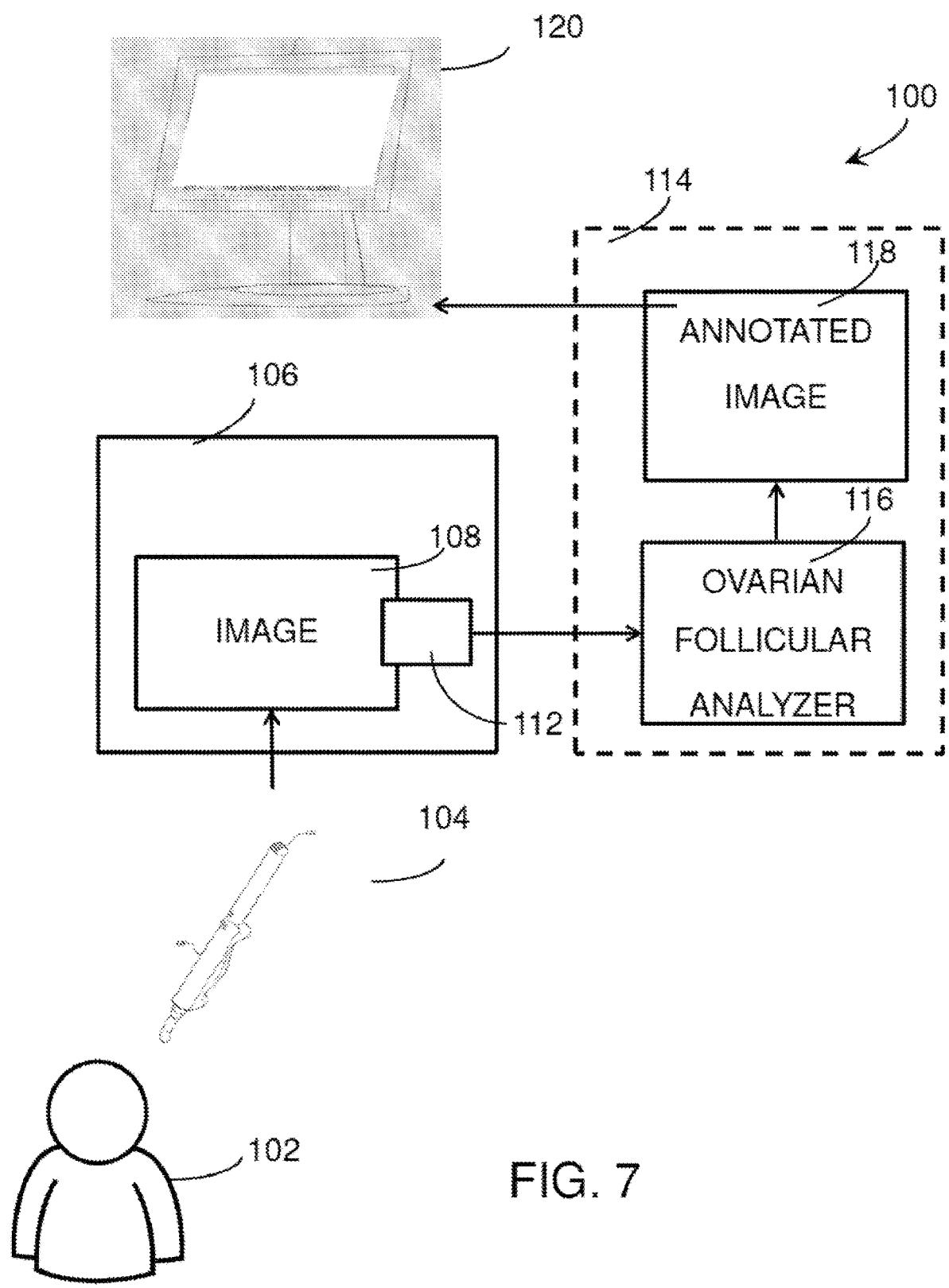
FIG. 7 is a schematic of an exemplary system that performs characterization of an ultrasound image.

FIG. 7 illustrates an exemplary embodiment of a system 100 for analyzing an ultrasound image. The system 100 includes an imaging sensor 104 that collects images from a subject 102 in a data receiving device 106 and is a component of and/or in communication with computing device 116 that functions to analyze the ultrasound image (i.e. ovarian follicular analyzer). Using techniques described herein, the system 100 may analyze an image of the imaging sensor 104 to produce an annotated image 118.

As shown in the example of FIG. 1, characterization system 114 includes computing device 116 for analyzing the image and producing annotated image 118. The computing device 116 receives data regarding a user input from the device 106. In some embodiments, computing device 116 may receive that data in the form of a raw image 108.

Characterization system 114 may be implemented in any suitable form. While characterization system 114 is illustrated in FIG. 1 as a separate computing device 116 from data receiving device 106, it should be appreciated that one or more components of the characterization system 114 may be part of data receiving device 106, computing device 116 and/or part of one or more other computing devices. In some embodiments, for example, the characterization system 114 may be implemented as a single stand-alone machine, or may be implemented by multiple distributed machines that share processing tasks in any suitable manner, that is/are separate from the computing device 116 and/or data receiving device 106 operated by the subject or user 102. The characterization system 114 may be implemented as one or more computers; an example of a suitable computer is described below. In some embodiments, the characterization system 114 may include one or more tangible, non-transitory computer-readable storage devices storing processor-executable instructions, and one or more processors that execute the processor-executable instructions to perform functions described herein. The storage devices may be implemented as computer-readable storage media (i.e., tangible, non-transitory computer-readable media) encoded with the processor-executable instructions; examples of suitable computer-readable storage media are discussed below.

Each of the processing components of the characterization system 114, including analyzer 116 may be implemented in software, hardware, or a combination of software and hardware. Components implemented in software may comprise sets of processor-executable instructions that may be executed by the one or more processors of the characterization system 114 to perform the functionality described herein. Each of the computing device 116 and image other data analyzers may be implemented as a separate component of the characterization system 114 (e.g., implemented by hardware and/or software code that is independent and performs dedicated functions of the component), or any combination of these components may be integrated into a single component or a set of distributed components (e.g., hardware and/or software code that performs two or more of the functions described herein may be integrated, the performance of shared code may be distributed among two or more hardware modules, etc.). In addition, any one of the analyzers or computing devices may be implemented as a set of multiple software and/or hardware components.

The annotated image 118 produced by the analyzer in the computing device 116 may be stored locally as a component of the system, and/or transmitted to a remote system for storage and/or displayed locally on a monitor 120.

Figure 8:
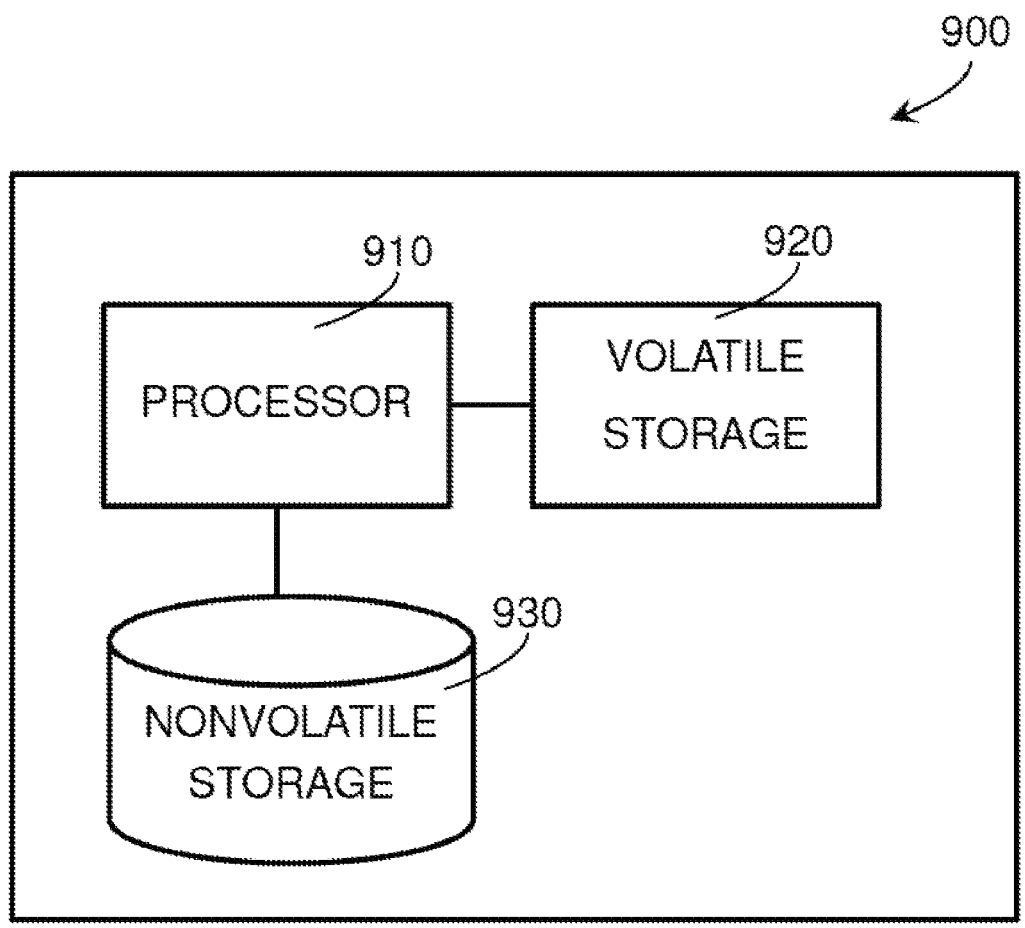
FIG. 8 is a block diagram of an exemplary computer system on which some embodiments may be implemented.

A system in accordance with the techniques described herein may take any suitable form, as embodiments are not limited in this respect. An illustrative implementation of a computer system 900 that may be used in connection with some embodiments is shown in FIG. 8. One or more computer systems such as computer system 900 may be used to implement any of the functionality described above. The computer system 900 may include one or more processors 910 and one or more computer-readable storage media (i.e., tangible, non-transitory computer-readable media), e.g., volatile storage 920 and one or more non-volatile storage media 930, which may be formed of any suitable data storage media. The processor 910 may control writing data to and reading data from the volatile storage 920 and the non-volatile storage device 930 in any suitable manner, as embodiments are not limited in this respect. To perform any of the functionality described herein, the processor 910 may execute one or more instructions stored in one or more computer-readable storage media (e.g., volatile storage 920 and/or non-volatile storage 930), which may serve as tangible, non-transitory computer-readable media storing instructions for execution by the processor 910.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation comprises at least one computer-readable storage medium (i.e., at least one tangible, non-transitory computer-readable medium), such as a computer memory (e.g., hard drive, flash memory, processor working memory, etc.), a floppy disk, an optical disk, a magnetic tape, or other tangible, non-transitory computer-readable medium, encoded with a computer program (i.e., a plurality of instructions), which, when executed on one or more processors, performs above-discussed functions. The computer-readable storage medium can be transportable such that the program stored thereon can be loaded onto any computer resource to implement techniques discussed herein. In addition, it should be appreciated that the reference to a computer program which, when executed, performs above-discussed functions, is not limited to an application program running on a host computer. Rather, the term "computer program" is used herein in a generic sense to reference any type of computer code (e.g., software or microcode) that can be employed to program one or more processors to implement above-techniques.

The phraseology and terminology used herein is for the purpose of description and should not be regarded as limiting. The use of "including," "comprising," "having," "containing," "involving," and variations thereof, is meant to encompass the items listed thereafter and additional items. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

Ovarian follicle monitoring has a number of primary measurement endpoints. In reproductive medicine, transvaginal ultrasound examination is primarily used for monitoring follicular growth during ovarian stimulation and for estimating ovarian reserve. The number and size of ovarian follicles, number of antral follicles (i.e. follicles that are 2-8 mm in average diameter), and growth rate of dominant follicles (i.e. follicles that are larger than 10 mm in average diameter) are the primary endpoints of measurement for ovarian follicle monitoring. Ovarian follicular monitoring is essential for guiding the amount and duration of medications for ovarian stimulation for ovulation induction and intrauterine insemination, controlled ovarian hyperstimulation for oocyte (egg) retrieval for in vitro fertilization (IVF), fresh embryo transfer, egg donation cycles, and for women who electively freeze their eggs or embryos for future use. Since measuring follicles is done manually and requires multiple visits, measuring follicles becomes tremendously inconvenient given the number of examinations that need to be done at fertility centers and hospitals. Moreover, ultrasound images analyzed by different technicians or medical experts can lead to inconsistent results and interpretations. Hence, the automated follicular monitoring of the invention has the great potential to maximize pregnancy success of IVF treatment on a large scale. Despite the clinical need for automated follicular monitoring, fully automated computerized follicular monitoring has not yet been achieved.

Thus, the invention is useful in some aspects for detecting changes in a person's body in order to collect information regarding a variety of conditions that may exist in the person, including ovarian dysfunction, normal or abnormal changes, cyclical or random within a body tissue. This type of information can be useful, for instance, alone or in combination with other detection/diagnostic methods to aid in diagnosing a condition, identifying early stages of disease, detecting changes in a condition influenced by environmental factors such as medicine or therapy, or detecting bodily changes to enhance fertility procedures.

Detection of disease associated with ovaries, ovarian follicles or other gynecological tissue is an important utility of the methods and devices of the invention. In some embodiments, the subject is undergoing a procedure comprising ovarian stimulation, ovulation induction, intrauterine insemination, controlled ovarian hyperstimulation, oocyte retrieval, in vitro fertilization, or embryo transfer.

In some embodiments, the subject has a reproductive condition or does not have a reproductive condition or infertility but is seeking elective fertility treatment for fertility preservation (e.g. oocyte and/or embryo cryopreservation). In other embodiments, the reproductive condition is due to infections, cancer, physical damage, or hormonal imbalances. In another embodiment, the reproductive condition comprises premature ovarian failure (POF), ovarian torsion, or polycystic ovarian syndrome (PCOS).

The methods and devices described herein can be used to detect properties associated with these disorders, often in earlier stages than the diseases can be detected by other methods. If a disease is detected using the methods of the invention, the presence of the disease or other properties such as the subtype or stage or degree of the disease can be further assessed by alternative methods known in the art. Alternatively if a disease is detected using other methodology it may be verified or further characterized using the methods of the invention. A number of properties associated with these diseases are well known in the art and may be used for further characterization.

The methods and devices described herein may also be used to assess the effectiveness of a therapeutic agent or putative therapeutic agent, by detecting changes in the disease state or progression. The methods and devices may also be used for evaluating or monitoring the state of the disease. The terms "assessing", "determining", "evaluating", "assaying" are used interchangeably herein to refer to any form of detection or measurement of a change, and include determining whether a change in degree of disease or condition, etc., is present or not. The result of an assessment may be expressed in qualitative and/or quantitative terms. Assessing may be relative or absolute.

Additionally, different people react differently to different therapeutic treatments. The methods and devices of the invention may be used to monitor an individual patients reaction to a particular therapeutic. Detecting, for instance changes in ovarian follicles.

In some embodiments, the subject is a human subject. The methods described herein are beneficial more analyzing images of a human body for many different purposes. For instance, any female subject requiring real-time ultrasound monitoring of ovaries in a clinical or remote setting, such as a home will benefit from the methods of the invention. The methods are useful for enhancing in vitro fertilization treatments, egg donors, fertility preservation treatment, etc. Thus, in some embodiments, the subject is of reproductive age and/or undergoing therapy to enhance reproduction.

In some embodiments, the subject is a non-human animal. The methods described herein are useful for assisting mammals with reproductive problems that require veterinary follicle monitoring for breeding management. Examples include but are not limited to sheep, horses, goats, cows, dogs, cats etc. In one embodiment, the non-human animal is a companion animal. Additionally, the methods and products described herein are useful for enhancing veterinary fertility therapy on endangered animals such as wild rare endangered mammals that require veterinary follicle monitoring for fertility preservations. For instance, elephants are trained from blood draws and ultrasound assessments and are used in veterinary assisted reproductive technologies as models for breeding management. Also pandas and dogs have been shown to respond successfully to in vitro fertilization techniques.

In some embodiments, the method further comprises measuring serum estrogen, anti-Mullerian hormone, progesterone, or testosterone levels in the subject. The combination of multiple diagnostic criteria can enhance the analysis of current status of the subject's body.

Having thus described several aspects of at least one embodiment of this invention, it is to be appreciated that various alterations, modifications, and improvements will readily occur to those skilled in the art.

Such alterations, modifications, and improvements are intended to be part of this disclosure, and are intended to be within the spirit and scope of the invention. Further, though advantages of the present invention are indicated, it should be appreciated that not every embodiment of the invention will include every described advantage. Some embodiments may not implement any features described as advantageous herein and in some instances. Accordingly, the foregoing description and drawings are by way of example only.

EXAMPLES

In various examples, it is illustrated that the methods, devices and algorithm described herein can successfully detect the follicles and outperform the conventional methods.

Methods

The methods use a rigorous image processing framework (FIG. 1) that overcomes the current limiting factors in real-time follicular monitoring. The framework was applied to ultrasound images of ovaries and successfully detected the follicles and outperformed the conventional methods (FIGS. 2-6) by overcoming the existing limiting factors in automated follicle detection. The images were inputted to the follicle detection algorithm in FIG. 1 and the algorithm detected the follicles as shown in FIGS. 2-6 automatically without any human input. The follicle detection algorithm shown in FIG. 1 as a flowchart allows for rapid identification of follicles while reducing the effect of noise and differentiating between the borders of adjacent follicles and the boundary between the follicle and ovarian stroma. Each step in the algorithm is not essential for the practice of the invention. The algorithm is exemplary.

Ultrasound Images

The ultrasound images used in this study were obtained from images published in [10] under CC BY 3.0 license. These images were inputted to the novel follicle detection algorithm of the invention as described herein to obtain the properties of follicles (such as their size, shape, and count) without requiring a technician or medical expert to detect or measure the follicles.

The data discussed below demonstrate that the methods and devices of the invention can successfully detect follicles in real-time using ultrasound images of ovaries and a reproducible computationally efficient quantitative image processing framework. The ultrasound images analyzed in these examples were compressed images obtained from images published online under CC BY 3.0 license. Digital Imaging and Communications in Medicine (DICOM) ultrasound images may also be examined. In order to apply the methods to DICOM images in a fast fully automated manner, the DICOM images may first be compressed such that they have similar complexity as the compressed images online. In order to reduce the complexity of the image, lossless (reversible) image compression techniques may be implemented (for example, by considering wavelet transform techniques) and then the compressed image may be inputted into the algorithm.

Example 1

In some ultrasound images, for some follicles, the areas that are closer to the follicle border are lighter than the rest of the follicle area. This can lead to not capturing the lighter areas of the follicle area as a part of the follicle. FIG. 2A is an example of such an ultrasound image. The image shown in FIG. 2A was processed using the analytical methods of the invention to produce an annotated ultrasound image, shown in FIG. 2B. FIG. 2B illustrates that this algorithm can successfully detect the entire follicle area (including the lighter areas of the follicle) (as opposed to not capturing the lighter areas of the follicle). Follicle detection was done in 2.1 seconds for this example.

Example 2

In some ultrasound images, for some follicles that are close to each other, the non-follicular area (ovarian stroma or tissue) between them might have an intensity level similar to the follicles, which can lead to detecting the entire region with follicles as one follicle region instead of identifying the individual follicles. FIG. 3A is an example of such an ultrasound image. The image shown in FIG. 3A was processed using the analytical methods of the invention to produce an annotated ultrasound image, shown in FIG. 3B. FIG. 3B illustrates that this algorithm can successfully detect individual follicles by differentiating between the borders of adjacent follicles and the boundary between the follicle and ovarian stroma. This was achieved in 2.3 seconds.

Example 3

Figure 4A:
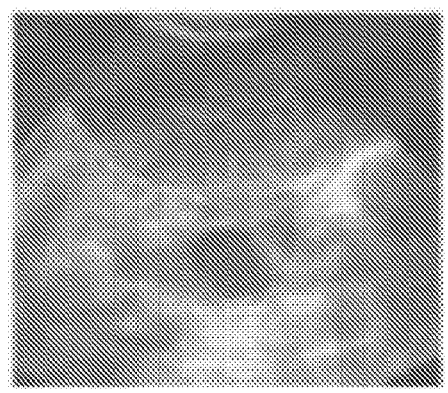
FIGS. 4A and 4B depict ultrasound images of Example 3 which show the ultrasound image of the ovary (FIG. 4A) and the detected follicle (FIG. 4B). The ultrasound image of 4A was published in [10] under CC BY 3.0 license.
Figure 4B:
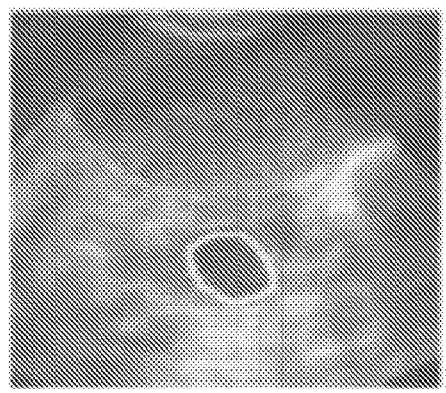

In some ultrasound images, the follicles are captured by lighter pixels compared to the usual ultrasound images. FIG. 4A is an example of such an ultrasound image. The image shown in FIG. 4A was processed using the analytical methods of the invention to produce an annotated ultrasound image, shown in FIG. 4B. FIG. 4B illustrates that this algorithm can successfully detect the follicle in such images. This was achieved in 2.3 seconds.

Example 4

Figure 5A:
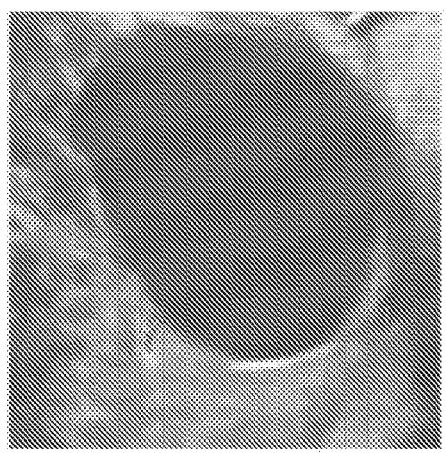
FIGS. 5A and 5B depict ultrasound images of Example 4 which show the ultrasound image of the ovary (FIG. 5A) and the detected cyst (FIG. 5B). The ultrasound image of 5A was published in [10] under CC BY 3.0 license.
Figure 5B:
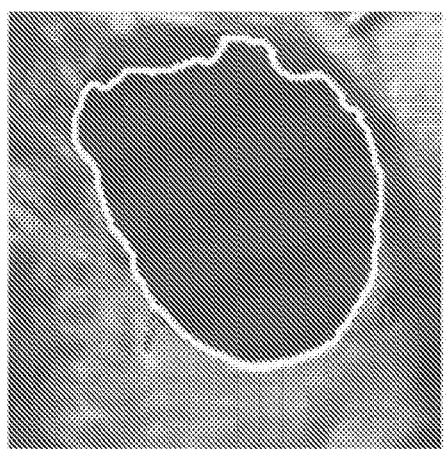

FIG. 5A is an example of an ultrasound image of a cystic ovary [10]. The image shown in FIG. 5A was processed using the analytical methods of the invention to produce an annotated ultrasound image, shown in FIG. 5B. FIG. 5B illustrates that this algorithm can successfully detect the large physiologic cyst which is not a follicle. This detection was achieved in 1.6 seconds.

Example 5

Figure 6A:
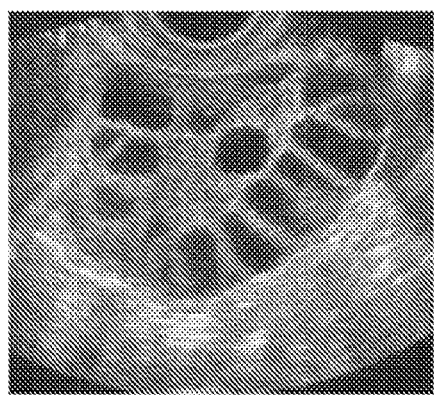
FIGS. 6A and 6B depict ultrasound images of Example 5 which show the ultrasound image of a polycystic ovary (FIG. 6A) and the detected follicles (FIG. 6B). The ultrasound image of 6A was published in [10] under CC BY 3.0 license.
Figure 6B:
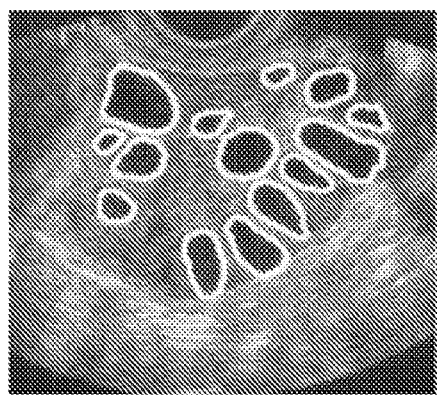

FIG. 6A is an example of an ultrasound image of an ovary with polycystic ovarian morphology (multiple peripherally distributed follicles with a central stromal prominence) in a patient with polycystic ovarian syndrome [17]. The image shown in FIG. 6A was processed using the analytical methods of the invention to produce an annotated ultrasound image, shown in FIG. 6B. FIG. 6B illustrates that this algorithm can successfully detect the follicles in this subset of patients. For this example, the runtime was 1.8 seconds.

REFERENCES

[1] Deutchman, Mark E., and Ricardo Hahn. "Obstetric ultrasonography." Primary Care: Clinics in Office Practice 24.2 (1997): 407-431.
[2] Lebbi, I., and R. Ben Temime. "The significance of monitoring folliculogenesis." IVF Lite 2.1 (2015): 6.
[3] Depmann, Martine, et al. "Fluctuations in anti-Müllerian hormone levels throughout the menstrual cycle parallel fluctuations in the antral follicle count: a cohort study." Acta obstetricia et gynecologica Scandinavica 95.7 (2016): 820-828.
[4] Hu, Xiaokun, et al. "New Perspectives on Criteria for the Determination of HCG Trigger Timing in GnRH Antagonist Cycles." Medicine 95.20 (2016).
[5] Potocnik, Bozidar, Boris Cigale, and Damj an Zazula. "Computerized detection and recognition of follicles in ovarian ultrasound images: a review." Medical & biological engineering & computing 50.12 (2012): 1201-1212.
[6] Ata, Baris, and Togas Tulandi. "Ultrasound automated volume calculation in reproduction and in pregnancy." Fertility and sterility 95.7 (2011): 2163-2170.
[7] Chatap, Niranjan J., and Ashish Kr Shrivastava. "A Survey on Various Classification Techniques for Medical Image Data." International Journal of Computer Applications 97.15 (2014).
[8] Rabiu, I. O., A. D. Usman, and A. M. S. Tekanyi. "A Review on Computer Assisted Follicle Detection Techniques and Polycystic Ovarian Syndrome (PCOS) Diagnostic Systems." International Journal of Computer Trends and Technology (IJCTT) 1.6 (2012).
[9] Hiremath, P. S., and Jyothi R. Tegnoor. "Automated ovarian classification in digital ultrasound images." International Journal of Biomedical Engineering and Technology 11.1 (2013): 46-65.
[10] Hiremath, P. S., and Jyothi R. Tegnoor. "Follicle detection and ovarian classification in digital ultrasound images of ovaries." Advancements and Breakthroughs in Ultrasound Imaging under CC BY 3.0 license, InTechOpen, UK (2013): 167-199.
[11] Kiruthika, V., and M. M. Ramya. "Automatic segmentation of ovarian follicle using K-means clustering." Signal and Image Processing (ICSIP), 2014 Fifth International Conference on. IEEE, 2014.
[12] Aja-Fernández, Santiago, and Carlos Alberola-López. "On the estimation of the coefficient of variation for anisotropic diffusion speckle filtering." IEEE Transactions on Image Processing 15.9 (2006): 2694-2701.
[13] Chan, Tony F., and Luminita A. Vese. "Active contours without edges." IEEE Transactions on image processing 10.2 (2001): 266-277.
[14] Li, Chunming, et al. "Distance regularized level set evolution and its application to image segmentation." IEEE Transactions on image processing 19.12 (2010): 3243-3254.
[15] Rosenfeld, Azriel, and John L. Pfaltz. "Sequential operations in digital picture processing." Journal of the ACM (JACM) 13.4 (1966): 471-494.
[16] Meyer, Fernand. "Topographic distance and watershed lines." Signal processing 38.1 (1994): 113-125.
[17] Khalid, Asma, and Tom Bourne. "Amenorrhoea and Polycystic Ovarian Syndrome." Ultrasound and Endoscopic Surgery in Obstetrics and Gynaecology. Springer London, 2003. 221-226.

The foregoing written specification is considered to be sufficient to enable one skilled in the art to practice the invention. The present invention is not limited in scope by the examples provided, since the examples are intended as illustrations of various aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

The invention claimed is:

1. A method of real-time ovarian follicular detection in a subject, comprising:
   a) obtaining ovarian ultrasound images of the subject's ovarian follicles using an ultrasound device,
   b) analyzing the ovarian ultrasound images with a segmentation algorithm to produce a fully annotated ultrasound image without manual input to allow for real-time ovarian follicular detection wherein the segmentation algorithm comprises hybrid segmentation methods comprising (1) a time-dependent partial differential equations (PDE) method for automatic detection of interior contours for locating follicle boundaries in presence of lighter pixels at follicle borders, (2) a gradient flow PDE approach for detecting topological changes, and (3) gradient flow approach for reaching a local minimum to differentiate between the borders of adjacent follicles.

2. The method of claim 1, wherein the subject is a human subject.

3. The method of claim 2, wherein the subject is of reproductive age.

4. The method of claim 2, wherein the subject is undergoing a procedure comprising ovarian stimulation, ovulation induction, intrauterine insemination, controlled ovarian hyperstimulation, oocyte retrieval, in vitro fertilization, or embryo transfer.

5. The method of claim 1, wherein the fully annotated ultrasound image includes identification and measurement of individual follicles and differentiates between the borders of adjacent follicles.

6. The method of claim 1, wherein the real time detection detects and measures all ovarian follicles in one ultrasound image in less than 30 seconds.

7. The method of claim 1, wherein the real time detection detects and measures all ovarian follicles in one ultrasound image in less than 10 seconds.

8. The method of claim 1, wherein the method of obtaining ovarian ultrasound images is performed by the subject remotely.

9. The method of claim 8, wherein the fully annotated ultrasound images are delivered to a health care provider.

10. The method of claim 1, wherein the segmentation algorithm involves analysis of the ovarian ultrasound images, by at least one processor, by producing a grayscale intensity image, producing a compressed image from the grayscale image, applying an anisotropic diffusion scheme for multiplicative speckle to reduce the speckle noise of the compressed image, rescaling and thresholding the compressed image to obtain a binary mask image, and performing morphological processing on the binary mask to obtain a morphologically processed mask.

11. The method of claim 10, further comprising labeling connected components in the morphologically processed mask.

12. The method of claim 11, further comprising, measuring properties of the morphologically processed mask, checking the properties of the labeled image regions to decide whether the labeled image region should be labeled as a follicle by considering physical constraints on some of the properties of the image region and generating a final binary mask that only includes image regions that are labeled as follicles and storing the properties of each of the labeled follicles.

13. The method of claim 10, wherein the production of the compressed image is performed using singular value decomposition on the grayscale image to produce the compressed image.

14. A method of real-time ovarian follicular detection in a subject, comprising:
   a) obtaining ovarian ultrasound images of the subject's ovarian follicles using an ultrasound device,
   b) analyzing the ovarian ultrasound images with a segmentation algorithm to produce a fully annotated ultrasound image without manual input to allow for real-time ovarian follicular detection, wherein the algorithm involves analysis of the ovarian ultrasound images, by at least one processor, by producing a grayscale intensity image, producing a compressed image from the grayscale image, applying an anisotropic diffusion scheme for multiplicative speckle to reduce the speckle noise of the compressed image, rescaling and thresholding the compressed image to obtain a binary mask image, and performing morphological processing on the binary mask to obtain a morphologically processed mask, wherein the production of the compressed image is performed using singular value decomposition on the grayscale image to produce the compressed image, wherein singular value decomposition is performed by calculating an explained variance for all possible approximation ranks in terms of a ratio of the Frobenius norm of a k-rank approximation matrix to a Frobenius norm of a full image matrix, wherein the k-rank approximation matrix that has the lowest rank among all approximation matrices that have an explained variance above a threshold is selected as a low rank approximation for obtaining the compressed image.

15. The method of claim 10, wherein anisotropic diffusion scheme is used with adaptive noise estimation over a square window.

16. A method of real-time ovarian follicular detection in a subject, comprising:
   a) obtaining ovarian ultrasound images of the subject's ovarian follicles using an ultrasound device,
   b) analyzing the ovarian ultrasound images with a segmentation algorithm to produce a fully annotated ultrasound image without manual input to allow for real-time ovarian follicular detection, wherein the algorithm involves analysis of the ovarian ultrasound images, by at least one processor, by producing a grayscale intensity image, producing a compressed image from the grayscale image, applying an anisotropic diffusion scheme for multiplicative speckle to reduce the speckle noise of the compressed image, rescaling and thresholding the compressed image to obtain a binary mask image, and performing morphological processing on the binary mask to obtain a morphologically processed mask, wherein when areas that are close to the follicle border are lighter than areas of the follicle further away from the follicle border an active contour method is used to create a second binary mask and wherein the second binary mask is combined with the binary mask image.

17. The method of claim 10, wherein morphological processing includes image dilation, followed by filling interior gaps, removing connected objects on follicle border, eroding the image, and removing small regions.

18. A method of real-time ovarian follicular detection in a subject, comprising:
   a) obtaining ovarian ultrasound images of the subject's ovarian follicles using an ultrasound device,
   b) analyzing the ovarian ultrasound images with a segmentation algorithm to produce a fully annotated ultrasound image without manual input to allow for real-time ovarian follicular detection,
   wherein the algorithm involves analysis of the ovarian ultrasound images, by at least one processor, by producing a grayscale intensity image, producing a compressed image from the grayscale image, applying an anisotropic diffusion scheme for multiplicative speckle to reduce the speckle noise of the compressed image, rescaling and thresholding the compressed image to obtain a binary mask image, and performing morphological processing on the binary mask to obtain a morphologically processed mask, wherein when the ovarian ultrasound images that are not very dark, the ovarian ultrasound images and the morphologically processed mask are inputted to a distance regularized level set evolution formulation, wherein the morphologically processed mask is an initial level set function to be updated by level set evolution, and wherein the obtained updated level set function after level set evolution is converted to a binary image.

19. The method of claim 18, wherein the level set evolution is derived as a gradient flow that minimizes an energy functional with a distance regularization term and an external energy that drives motion of a zero level set toward desired locations.

20. The method of claim 19, wherein the distance regularization term has a double-well potential function which forces the gradient magnitude of the level set function a minimum point.

21. A method of real-time ovarian follicular detection in a subject, comprising:
   a) obtaining ovarian ultrasound images of the subject's ovarian follicles using an ultrasound device,
   b) analyzing the ovarian ultrasound images with a segmentation algorithm to produce a fully annotated ultrasound image without manual input to allow for real-time ovarian follicular detection,
   wherein the algorithm involves analysis of the ovarian ultrasound images, by at least one processor, by producing a grayscale intensity image, producing a compressed image from the grayscale image, applying an anisotropic diffusion scheme for multiplicative speckle to reduce the speckle noise of the compressed image, rescaling and thresholding the compressed image to obtain a binary mask image, and performing morphological processing on the binary mask to obtain a morphologically processed mask, further comprising distance transforming white areas having area threshold properties in the binary image mask using a Chebyshev distance transform to perform watershed segmentation and produce an output, wherein the pixels having highest gradient magnitude intensities represent follicle region boundaries and gradient of an image flows along a path to finally reach a local minimum which represents a segment and wherein the output of the watershed segmentation and the white areas in the binary image mask that are less than the area threshold properties are combined to generate a watershed segmented binary image.

22. The method of claim 1, wherein the subject has a reproductive condition or does not have a reproductive condition or infertility but is seeking elective fertility treatment for fertility preservation (e.g. oocyte and/or embryo cryopreservation).

23. The method of claim 22, wherein the reproductive condition is due to infections, cancer, physical damage, or hormonal imbalances.

24. The method of claim 23, wherein the reproductive condition comprises premature ovarian failure (POF), ovarian torsion, or polycystic ovarian syndrome (PCOS).

25. The method of claim 1, wherein the subject is a non-human animal.

26. An automated follicular detection sonogram system comprising:
    an imaging sensor for obtaining an ultrasound image, sequence of ultrasound images or ultrasound video of an ovary of a subject,
    at least one computer-readable storage medium storing computer-executable instructions that, when executed, perform a method for automatic detection of ovarian follicles by analyzing an ultrasound image, sequence of ultrasound images or ultrasound video, the method comprising:
    receiving the ultrasound image, sequence of ultrasound images or ultrasound video obtained from a subject;
    determining, measuring and labeling, by at least one processor, individual follicles within the ultrasound image, sequence of ultrasound images or ultrasound video, wherein the individual follicles are differentiated from adjacent follicles, wherein the individual follicles are determined, measured and labeled by converting the ultrasound image, sequence of ultrasound images or ultrasound video to a grayscale intensity image, compressing the grayscale intensity image using a singular value decomposition to form a compressed image, reducing speckle noise of the compressed image to produce a reduced noise image, processing the reduced noise image to produce a binary mask image, performing morphological processing on the binary mask image to obtain a morphologically processed mask, and labeling and measuring follicles imaged within the morphologically processed mask to produce a fully annotated ultrasound image, images or video, wherein when areas that are close to the follicle border are lighter than areas of the follicle further away from the follicle border an active contour method is used to create a second binary mask and wherein the second binary mask is combined with the binary mask image and
    performing automatic detection of ovarian follicles at least in part by analyzing at least the fully annotated ultrasound image, images or video without manual input.

27. An automated follicular detection sonogram system comprising:
    an imaging sensor for obtaining an ultrasound image, sequence of ultrasound images or ultrasound video of an ovary of a subject, wherein the ovarian ultrasound images are obtained with a segmentation algorithm to produce a fully annotated ultrasound image without manual input to allow for real-time ovarian follicular detection wherein the segmentation algorithm comprises hybrid segmentation methods comprising (1) a time-dependent partial differential equations (PDE) method for automatic detection of interior contours for locating follicle boundaries in presence of lighter pixels at follicle borders, (2) a gradient flow PDE approach for detecting topological changes, and (3) gradient flow approach for reaching a local minimum to differentiate between the borders of adjacent follicles,
    a storage device for storing the ultrasound image, sequence of ultrasound images or ultrasound video locally or remotely, and
    at least one computer-readable storage medium storing computer-executable instructions that, when executed, perform automated detection and measurement of ovarian follicles within the stored ultrasound image, sequence of ultrasound images or ultrasound video to produce a fully annotated ultrasound image.

\* \* \* \* \*